(12) United States Patent
Chein et al.

(10) Patent No.: US 10,392,357 B2
(45) Date of Patent: Aug. 27, 2019

(54) GLUCAGON-LIKE PEPTIDE 1 MODULATOR AND USES THEREOF

(71) Applicant: Academia Sinica, Taipei (TW)

(72) Inventors: Rong-Jie Chein, Taipei (TW); Klim King, Taipei (TW); Nai-Pin Lin, Taipei (TW); Yu-Hong Cheng, Taipei (TW)

(73) Assignee: Acaemia Sinica, Taipei (TW)

( * ) Notice: Subject to any disclaimer, the term of this patent is extended or adjusted under 35 U.S.C. 154(b) by 0 days.

(21) Appl. No.: 15/576,307

(22) PCT Filed: Jun. 30, 2016

(86) PCT No.: PCT/US2016/040225
§ 371 (c)(1),
(2) Date: Nov. 22, 2017

(87) PCT Pub. No.: WO2017/004283
PCT Pub. Date: Jan. 5, 2017

(65) Prior Publication Data
US 2018/0179172 A1    Jun. 28, 2018

Related U.S. Application Data

(60) Provisional application No. 62/186,512, filed on Jun. 30, 2015.

(51) Int. Cl.
| | |
|---|---|
| *C07D 307/22* | (2006.01) |
| *C07D 307/33* | (2006.01) |
| *C07D 307/83* | (2006.01) |
| *C07D 333/32* | (2006.01) |
| *C07D 333/36* | (2006.01) |
| *A61K 31/155* | (2006.01) |
| *A61K 31/365* | (2006.01) |
| *A61K 31/366* | (2006.01) |
| *A61K 31/4439* | (2006.01) |
| *A61K 31/48* | (2006.01) |
| *A61K 31/4985* | (2006.01) |
| *A61K 31/64* | (2006.01) |
| *A61K 31/702* | (2006.01) |
| *A61K 31/7042* | (2006.01) |
| *A61K 45/06* | (2006.01) |

(52) U.S. Cl.
CPC .......... *C07D 307/22* (2013.01); *A61K 31/155* (2013.01); *A61K 31/365* (2013.01); *A61K 31/366* (2013.01); *A61K 31/4439* (2013.01); *A61K 31/48* (2013.01); *A61K 31/4985* (2013.01); *A61K 31/64* (2013.01); *A61K 31/702* (2013.01); *A61K 31/7042* (2013.01); *A61K 45/06* (2013.01); *C07D 307/33* (2013.01); *C07D 307/83* (2013.01); *C07D 333/32* (2013.01); *C07D 333/36* (2013.01)

(58) Field of Classification Search
CPC .. C07D 307/22; C07D 307/33; C07D 307/83; C07D 333/32; C07D 333/36; A61K 31/155; A61K 31/365; A61K 31/366; A61K 31/4439; A61K 31/48; A61K 31/4985; A61K 31/64; A61K 31/702; A61K 31/7042; A61K 45/06
See application file for complete search history.

(56) References Cited

PUBLICATIONS

McCully et al., 23(1) Chemotherapy (Basel, Switzerland) 44-9 (1977) (CAS Abstract) (Year: 1977).*
Puskas et al., 179(23) J. of Bacteriology 7530-7537 (1997) (CAS Abstract) (Year: 1997).*
Anselmetti et al., 24(4) Langmuir 1365-1370 (2008) (CAS Abstract) (Year: 2008).*
Kraatz et al., 744 Justus Liebigs Annalen der Chemie 33-41 (1971) (CAS Abstract) (Year: 1971).*

* cited by examiner

*Primary Examiner* — Timothy R Rozof

(57) ABSTRACT

Disclosed herein are novel glucagon-like peptide-1 (GLP-1) modulators and their uses in manufacturing medicaments for the treatment and/or prophylaxis of diseases and/or disorders associated with hyperglycemia.

16 Claims, 6 Drawing Sheets

(A)

(B)

(A)

(B)

GLUCAGON-LIKE PEPTIDE 1 MODULATOR AND USES THEREOF

CROSS REFERENCES

This application is a national stage of PCT/US16/40225 filed Jun. 30, 2016, which claims priority to U.S. Provisional Application No. 62/186,512, filed Jun. 30, 2015, the disclosure of which are incorporated herein by reference in its entirety.

BACKGROUND OF THE INVENTION

1. Field of the Invention

The present disclosure in general relates to the field of treatment of hyperglycemia; more particularly to the novel glucagon like peptide 1 modulators, and their uses in the treatment or prophylaxis of diseases and/or disorders associated with hyperglycemia.

2. Description of Related Art

High blood sugar (or hyperglycemia) is a condition in which an excessive amount of glucose circulates in the blood plasma. Hyperglycemia is most commonly caused by diabetes mellitus that is increasingly prevalent and results in a high frequency of complications that lead to a significant reduction of life quality and expectancy. Because of diabetes-associated microvascular complications, type 2 diabetes is currently the most frequent cause of adult-onset loss of vision, renal failure, and amputations in the industrialized world. In addition, the presence of type 2 diabetes is associated with a 2 to 5 folds increase in cardiovascular disease risk. Diabetes is also a leading cause of damage to the retina at the back of the eye and increases risk of cataracts and glaucoma. Diabetes has also been implicated in the development of kidney disease and with nerve damage, especially in the legs and feet, which interferes with the ability to sense pain and contributes to serious infections. Taken together, diabetes-associated complications are among the leading causes of morbidity and mortality worldwide.

"Good glycemic control" is characterized by maintaining blood glucose levels within acceptable limits and by minimizing fluctuations outside of normal limits between treatments. Persistent poor glycemic control increases the risk of long-term vascular complications of diabetes such as coronary disease, heart attack, stroke, heart failure, kidney failure, blindness, neuropathy (loss of sensation, especially in the feet), and gangrene. Poor glycemic control also increases the risk of short-term complications of surgery such as poor wound healing.

Traditional therapeutic drugs for the treatment of type-2 diabetes, such as metformin, sulfonylureas or insulin, do not always provide good glycemic control. Two new drug classes have been developed: glucagon-like peptide (GLP)-1 receptor (GLP-1R) agonist, and dipeptidyl peptidase 4 (DPP-4) inhibitor. Currently, two GLP-1R agonists are available, they are exenatide and liraglutide, with several more currently being developed. DPP-4 inhibitor class exemplified by sitagliptin, alogliptin, and saxagliptin.

Although these therapeutic drugs can bring blood glucose levels within normal limits in many patients with hyperglycemia, there are many patients with poor glycemic control and are in need of alternative treatment, Therefore, there is an unmet medical need for new therapeutic agents with new mechanisms of action, that are safe and effective for improving glycemic control in patients with hyperglycemia.

SUMMARY

The present disclosure is based on unexpected discovery that certain compounds are potent GLP-1 receptor (GLP-1R) modulators that bind to GLP-1 and enhance the activation of GLP-1R signaling, these compounds are thus useful for the development of medicaments for treating diseases and/or disorders associated with hyperglycemia (e.g., type 2 diabetes, obesity and etc.).

Accordingly, one aspect of the present disclosure is to provide a novel compound having the structure of formula (I),

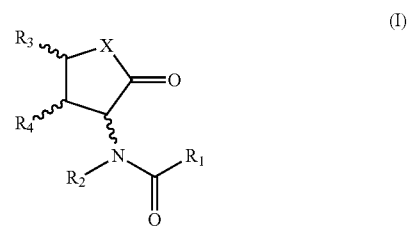

wherein:
  X is O or S;
  $R_1$ is H or

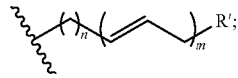

$R_2$ is H or a nitrogen protecting group;
  $R_3$ and $R_4$ are independently H, halogen, optionally substituted alkyl or alkenyl; or $R_3$ and $R_4$ are taken together to form an optionally substituted 6-membered carbocycle or heterocycle;
  R' is H or optionally substituted alkyl; and
  n and m are independently an integral between 1 to 10.

According to one preferred embodiment, the compound of formula (I) is

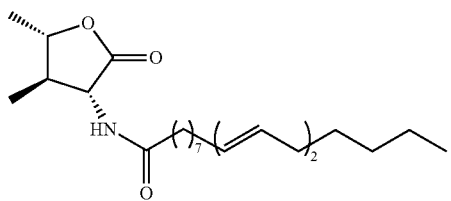

A further aspect of the present disclosure is to provide a pharmaceutical composition for the treatment or prophylaxis of a subject having or suspected of having diseases and/or disorders associated with hyperglycemia. The pharmaceutical composition comprises a therapeutically or prophylactically effective amount of the compound of formula (I); and a pharmaceutically acceptable carrier.

The compound of formula (I) is present at a level of about 0.1% to 99% by weight, based on the total weight of the pharmaceutical composition. In some embodiments, the compound of formula (I) is present at a level of at least 1% by weight, based on the total weight of the pharmaceutical composition. In certain embodiments, the compound of formula (I) is present at a level of at least 5% by weight, based on the total weight of the pharmaceutical composition. In still other embodiments, the compound of formula (I) is present at a level of at least 10% by weight, based on the total weight of the pharmaceutical composition. In still yet other embodiments, the compound of formula (I) is present at a level of at least 25% by weight, based on the total weight of the pharmaceutical composition.

According to some preferred embodiments, the pharmaceutical composition further comprises a blood sugar reducing agent, which is selected to from the group consisting of, alpha-glucosidase inhibitor, biguanide, dopamine agonist, dipeptidyl peptidase-4 (DPP-4) inhibitor, glucagon-like peptide-1 (GLP-1), meglitinide, sodium glucose transporter (SGLT) 2 inhibitor, sulfonylurea, and thiazolidinedione.

The present disclosure also encompasses a method for the treatment or prophylaxis of a subject having or suspected of having a disease and/or disorder associated with hyperglycemia. The method comprises the step of administering a therapeutically or prophylactically effective amount of the compound of formula (I) to the subject, so as to ameliorate, mitigate and/or prevent the symptoms of the disease and/or disorder.

According to some preferred embodiments, the method further includes the step of administering to the subject another agent that is known to reduce the blood sugar level in the subject, such as an alpha-glucosidase inhibitor, biguanide, dopamine agonist, dipeptidyl peptidase-4 (DPP-4) inhibitor, glucagon-like peptide-1 (GLP-1), meglitinide, sodium glucose transporter (SGLT) 2 inhibitor, sulfonylurea, and thiazolidinedion, before, together with, or after the administration of the compound of formula (I) of the present invention.

The present disclosure also encompasses kits useful for the treatment or prophylaxis of a subject having or suspected of having a disease and/or disorder associated with hyperglycemia. The kit include, at least, a first container containing a blood sugar reducing agent; and a second container containing the present compound of formula (I).

The details of one or more embodiments of this disclosure are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

BRIEF DESCRIPTION OF THE DRAWINGS

The accompanying drawings, which are incorporated in and constitute a part of the specification, illustrate various example systems, methods and other exemplified embodiments of various aspects of the invention. The present description will be better understood from the following detailed description read in light of the accompanying drawings, where.

DETAILED DESCRIPTION OF THE PREFERRED EMBODIMENTS

Figure 1A:
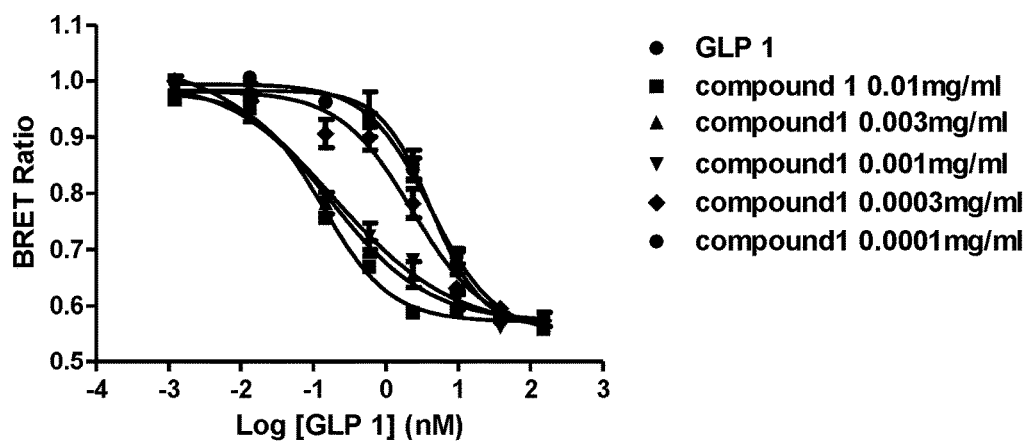
FIG. 1A illustrates the effect of compound 1 enhancing GLP-1 induced cAMP production in RINm5F cells in according to one embodiment of the present disclosure.
Figure 1B:
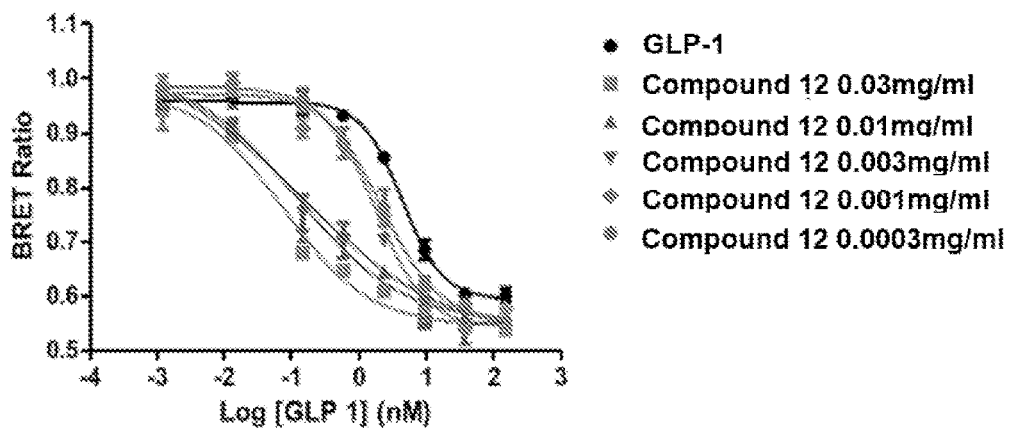
FIG. 1B illustrates the effect of compound 12 enhancing GLP-1 induced cAMP production in RINm5F cells in according to one embodiment of the present disclosure.
Figure 1C:
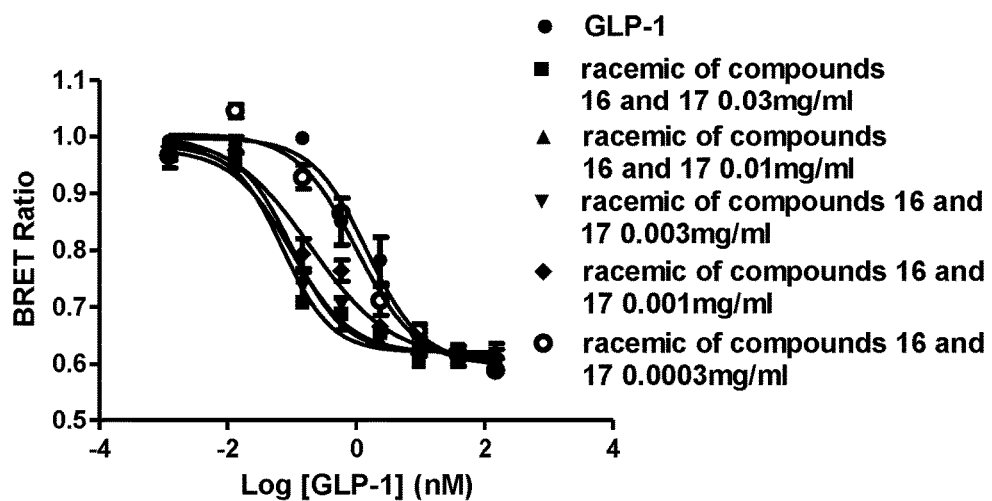
FIG. 1C illustrates the effect of a racemic mixture of compounds 16 and 17 enhancing GLP-1 induced cAMP production in RINm5F cells in according to one embodiment of the present disclosure.
Figure 1D:
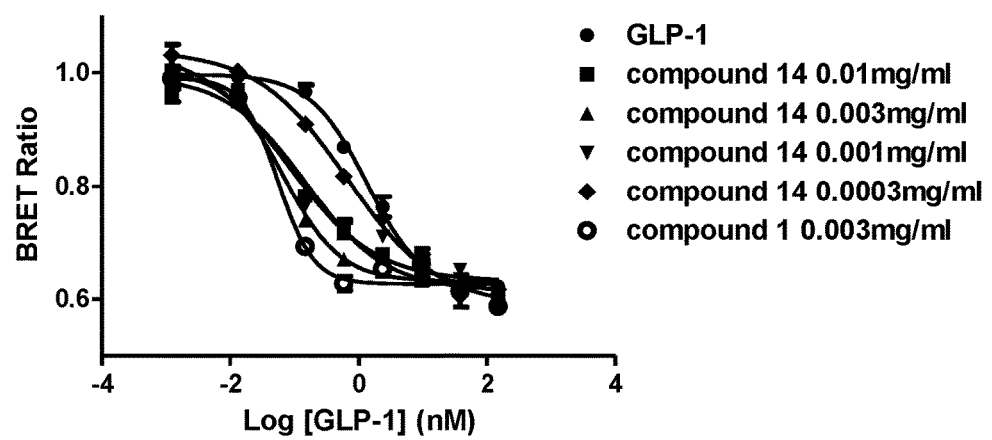
FIG. 1D illustrates the effect of compound 14 enhancing GLP-1 induced cAMP production in RINm5F cells in according to one embodiment of the present disclosure.
Figure 1E:
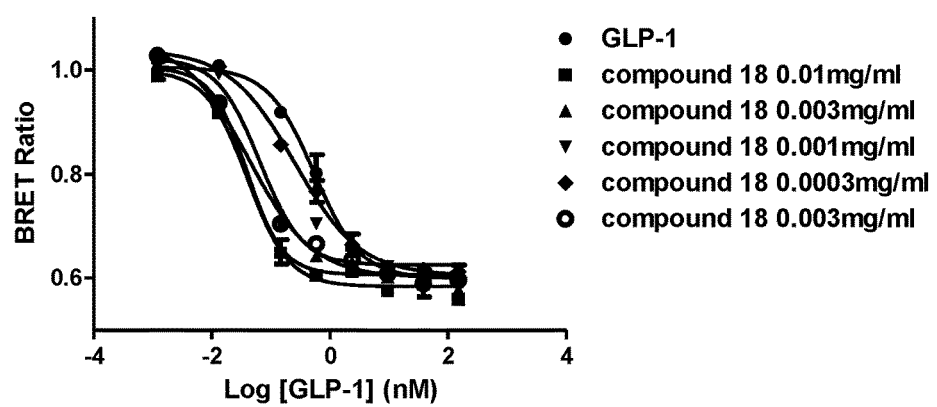
FIG. 1E illustrates the effect of compound 18 enhancing GLP-1 induced cAMP production in RINm5F cells in according to one embodiment of the present disclosure.

The detailed description provided below in connection with the appended drawings is intended as a description of the present disclosure and is not intended to represent the only forms in which the present disclosure may be constructed or utilized.

1. Definitions

Unless otherwise indicated, the term "alkyl" means a straight or branched hydrocarbon having from 1 to 23 carbon atoms, e.g., 1, 2, 3, 4, 5, 6, 7, 8, 9, 10, 11, 12, 13, 14, 15, 16, 17, 18, 19, 20, 21 or 23 carbon atoms. Unless otherwise specified, each instance of an alkyl group is independently optionally substituted, i.e., unsubstituted (an "unsubstituted alkyl") or substituted (a "substituted alkyl") with one or more substituents.

Unless otherwise indicated, the term "alkenyl" means a straight or branched hydrocarbon having from 2 to 23 carbon atoms (e.g., 2, 3, 4, 5, 6, 7, 8, 9, 10, 11, 12, 13, 14, 15, 16, 17, 18, 19, 20, 21, 22 or 23 carbon atoms), and including one or more carbon-carbon double bond (e.g., 1, 2, 3, 4, 5, 6, or 7 carbon-carbon double bonds). The one or more carbon-carbon double bonds can be internal (such as in 2-butenyl) or terminal (such as in 1-butenyl). Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is $C_{15}$ alkenyl having one carbon-carbon double bond. In certain embodiments, the alkenyl group is $C_{17}$ alkenyl having 2 or 3 carbon-carbon double bonds. In certain embodiments, the alkenyl group is $C_{19}$ alkenyl having 4 or 5 carbon-carbon double bonds. In certain embodiments, the alkenyl group is $C_{21}$ alkenyl having 6 carbon-carbon double bonds.

Unless otherwise indicated, the term "carbocycle" means a cycloalkyl or cycloalkenyl moiety. In certain embodiment, the carbocycle is a cyclohexyl moiety.

Unless otherwise indicated, the term "heterocycle" means a cycloalkyl or cycloalkenyl moiety wherein at least one of its carbon atoms has been replaced with a heteroatom (e.g., N, O or S). Examples include, but are not limited to, benzofuranyl, benzothienyl, quinolyl, benzodioxolyl, furyl, and thienyl.

Unless otherwise indicated, the terms "halogen" and "halo" encompass fluoro, chloro, bromo, and iodo.

Unless otherwise indicated, the term "substituted," when used to describe a chemical structure or moiety, refers to a derivative of that structure or moiety wherein one or more of its hydrogen atoms is substituted with an atom, chemical moiety or functional group such as, but not limited to, —OH, —CHO, alkoxy, alkanoyloxy (e.g., —OAc), alkenyl, alkyl (e.g., methyl, ethyl, propyl, t-butyl), aryl, aryloxy, halo, or haloalkyl (e.g., —CCl$_3$, —CF$_3$, —C(CF$_3$)$_3$). Unless otherwise indicated, the term "alkoxy" means an —O-alkyl group. Examples of alkoxy groups include, but are not limited to, —OCH$_3$, —OCH$_2$CH$_3$, —O(CH$_2$)$_2$CH$_3$, —O(CH$_2$)$_3$CH$_3$, —O(CH$_2$)$_4$CH$_3$, and —O(CH$_2$)$_5$CH$_3$. The term "lower alkoxy" refers to —O-(lower alkyl), such as —OCH$_3$ and —OCH$_2$CH$_3$.

Unless otherwise indicated, "nitrogen protecting group" includes, but is not limited to, alkyl, alkenyl, alkynyl, —OH, —OR$^a$, —C(=O)R$^a$, —CO$_2$R$^a$, —SOR$^a$, —SO$_2$R$^a$, and —SO$_2$OR$^a$, in which R$^a$ refers to alkyl, alkenyl, aryl, aralkyl, carbocycle, heterocycle, or heteroaryl. Nitrogen protecting groups are well known in the art and include those described in detail in *Protecting Groups in Organic Synthesis*, T. W. Greene and P. G. M. Wuts, 3$^{rd}$ Edition, John Wiley & Sons, 1999, which is incorporated herein by reference.

Unless otherwise indicated, one or more adjectives immediately preceding a series of nouns is to be construed as applying to each of the nouns. For example, the phrase "optionally substituted alky, alkenyl, carbocycle or heterocycle" has the same meaning as "optionally substituted alky, optionally substituted alkenyl, optionally substituted carbocycle, or optionally substituted heterocycle."

For purpose of this invention, heteroatoms such as nitrogen may have hydrogen substituents and/or any suitable substituents as described herein which satisfy the valencies of the heteroatoms and result in the formation of a stable moiety.

Unless otherwise indicated, a "therapeutically effective amount" of a compound is an amount sufficient to provide a therapeutic benefit in the treatment or management of a disease or condition, or to delay or minimize one or more symptoms associated with the disease or condition. A therapeutically effective amount of a compound is an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, a "prophylactically effective amount" of a compound is an amount sufficient to prevent a disease or condition, or one or more symptoms associated with the disease or condition, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

Unless otherwise indicated, the terms "treat," "treating" and "treatment" contemplate an action that occurs while a patient is suffering from the specified disease or disorder, which reduces the severity of the disease or disorder, or one or more of its symptoms, or retards or slows the progression of the disease or disorder.

It should also be noted that if the stereochemistry of a structure or a portion of a structure is not indicated with, for example, bold or dashed lines, the structure or the portion of the structure is to be interpreted as encompassing all stereoisomers of it. Similarly, names of compounds having one or more chiral centers that do not specify the stereochemistry of those centers encompass pure stereoisomers and mixtures thereof. Moreover, any atom shown in a drawing with unsatisfied valences is assumed to be attached to enough hydrogen atoms to satisfy the valences.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The singular forms "a", "and", and "the" are used herein to include plural referents unless the context clearly dictates otherwise.

2. Novel Compounds of Formula (I)

This invention encompasses compounds of formula (I),

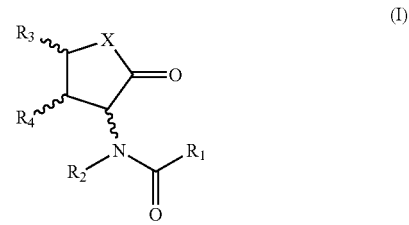

wherein:
 X is O or S;
 R$_1$ is H or

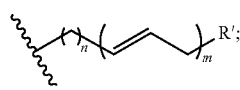

R$_2$ is H or a nitrogen protecting group;
 R$_3$ and R$_4$ are independently H, halogen, optionally substituted alkyl or alkenyl; or R$_3$ and R$_4$ are taken together to form an optionally substituted carbocycle or heterocycle;
 R' is H or optionally substituted alkyl; and
 n and m are independently an integral between 1 to 10.

According to one preferred embodiment, the compound of formula (I) is

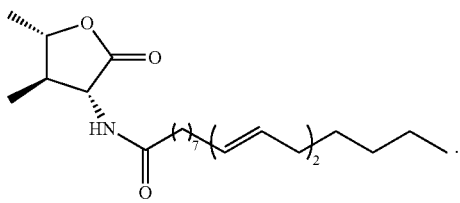

Compounds of the invention contain one or more stereocenters, thus can exist as racemic mixtures of enantiomers or mixtures of diastereomers. This invention thus encompasses stereomerically pure forms of such compounds, as well as mixtures of those forms. Stereoisomers may be asymmetrically synthesized or resolved using standard techniques such as crystallization, chromatography, and the use of a resolving agent. One preferred way of separating enantiomers from a racemic mixture is by use of preparative high performance liquid chromatography (HPLC). Alternatively, the racemic may be separated into its enantiomers by reacting with an optically active form of a resolving agent in the presence of a solvent. Depending on the optical form of the resolving agent, one of the two enantiomers is separated out as an insoluble salt with high yield and high optical purity, while the opposite enantiomer remains in the solution.

The present invention thus further encompasses stereoisomeric mixtures of compounds disclosed herein. It also encompasses configurational isomers of compounds disclosed herein (e.g., cis and trans isomers, whether or not involving double bonds), either in admixture or in pure or substantially pure form.

According to certain embodiments, particular compounds of formula (I) has the structure of formula (I-1),

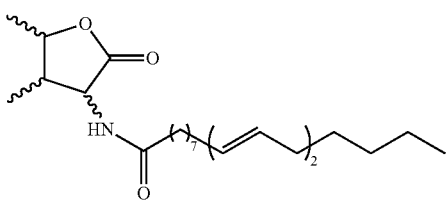
(I-1)

Exemplary compounds of formula (I-1) described herein include, but are not limited to,

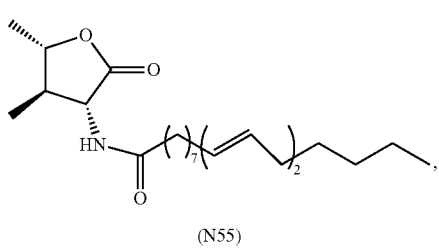
(N55)

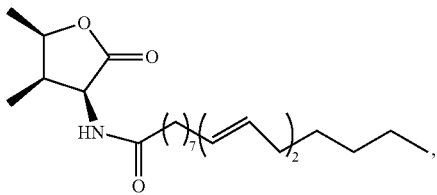
2

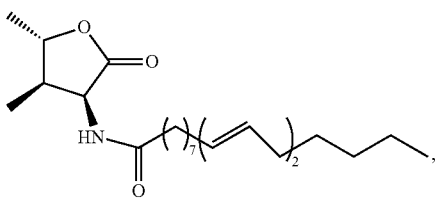
3

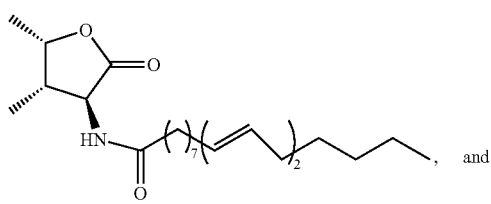
4, and

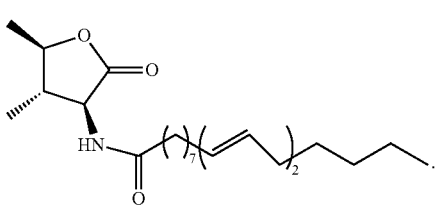
5

According to certain embodiments, particular compounds of formula (I) has the structure of formula (I-2),

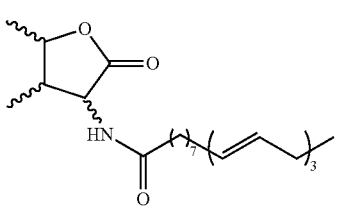
(I-2)

Exemplary compounds of formula (I-2) described herein include, but are not limited to,

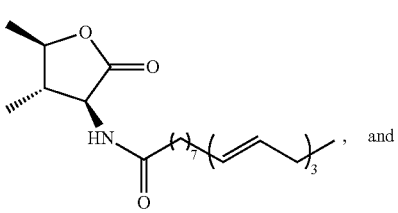
6, and

-continued

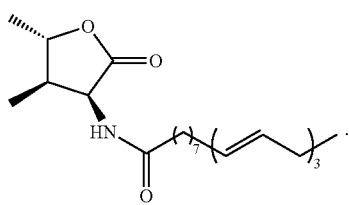
7

According to certain embodiments, particular compounds of formula (I) has the structure of formula (I-3), (I-3)

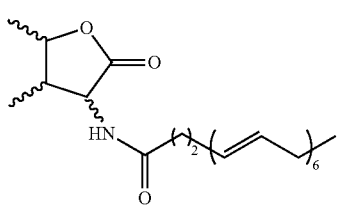

Exemplary compounds of formula (I-3) described herein include, but are not limited to,

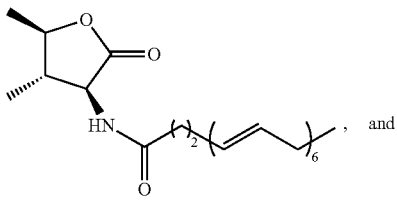
8 , and

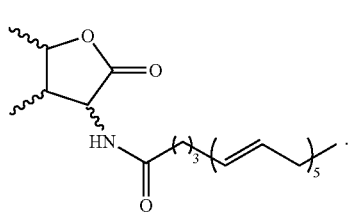
9

According to certain embodiments, particular compounds of formula (I) has the structure of formula (I-4), (I-4)

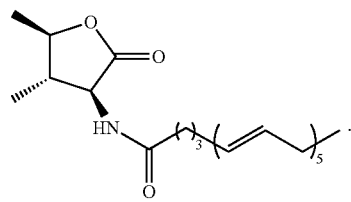
10

According to certain embodiments, particular compounds of formula (I) has the structure of formula (I-5), (I-5)

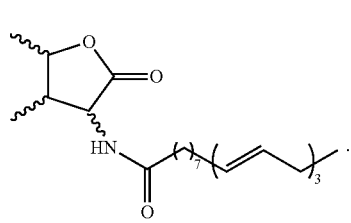

Exemplary compound of formula (I-5) described herein includes, but is not limited to,

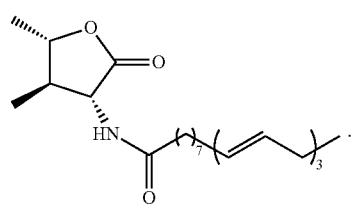
11

According to certain embodiments, particular compounds of formula (I) has the structure of formula (I-6), (I-6)

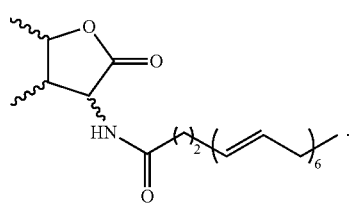

Exemplary compound of formula (I-6) described herein includes, but is not limited to,

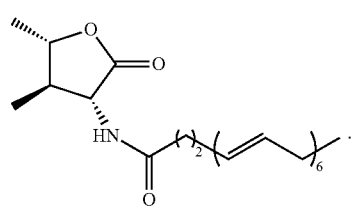
12

According to certain embodiments, particular compounds of formula (I) has the structure of formula (I-7), Exemplary compound of formula (I-4) described herein includes, but is not limited to, (I-7)

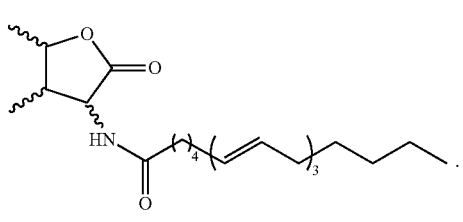

Exemplary compound of formula (I-7) described herein includes, but is not limited to,

13

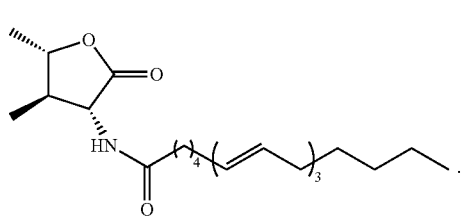

According to certain embodiments, particular compounds of formula (I) has the structure of formula (I-8), (I-8)

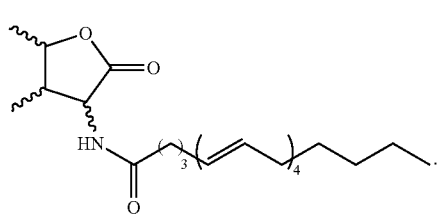

Exemplary compound of formula (I-8) described herein includes, but is not limited to,

14

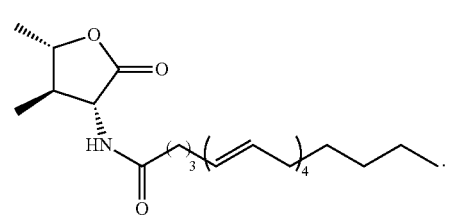

According to certain embodiments, particular compounds of formula (I) has the structure of formula (I-9), (I-9)

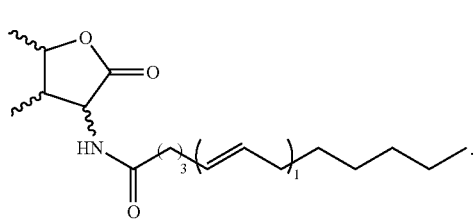

Exemplary compound of formula (I-9) described herein includes, but is not limited to,

15

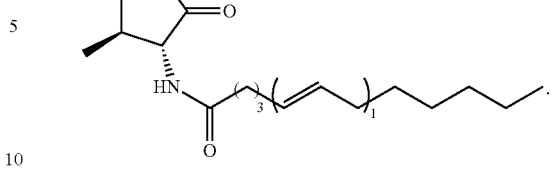

According to certain embodiments, particular compounds of formula (I) has the structure of formula (I-10), (I-10)

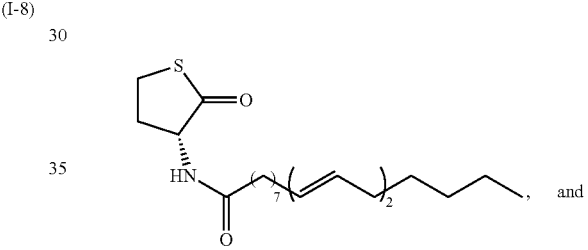

Exemplary compounds of formula (I-10) described herein include, but are not limited to,

16

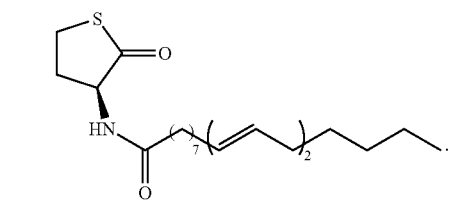

, and

17

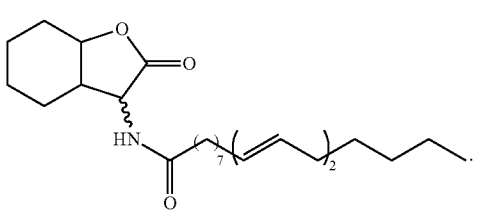

According to certain embodiments, particular compounds of formula (I) has the structure of formula (I-11), (I-11)

Exemplary compounds of formula (I-10) described herein include, but are not limited to,

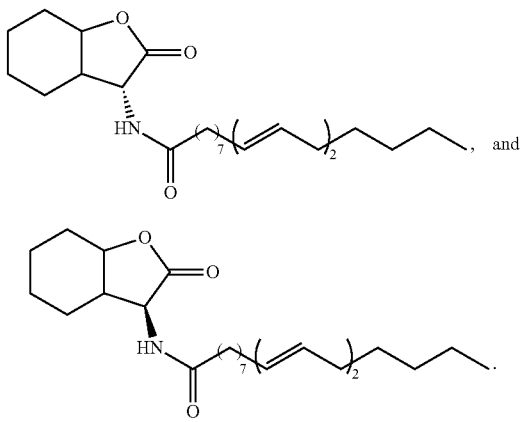

3. Method of Use

The present invention encompasses a method for the treatment or prophylaxis of a subject having or suspected of having a disease and/or disorder associated with hyperglycemia. The method comprises the step of administering a therapeutically or prophylactically effective amount of the compound of formula (I) of the present disclosure to the subject, so as to reduce the blood sugar level of the subject, thereby ameliorates, mitigates and/or prevents the symptoms of the disease and/or disorder associated with hyperglycemia.

In some embodiments, the method further includes the step of administering to the subject a blood sugar reducing agent, before, together with, or after the administration of the compound of formula (I). The blood sugar reducing agent may be selected from the group consisting of, alpha-glucosidase inhibitor, biguanide, dopamine agonist, dipeptidyl peptidase-4 (DPP-4) inhibitor, glucagon-like peptide-1 (GLP-1), meglitinide, sodium glucose transporter (SGLT) 2 inhibitor, sulfonylurea, and thiazolidinedione.

According to embodiments of the present disclosure, the alpha-glucosidase inhibitor is acarbose or miglitol. Suitable example of the biguanide is metformin. Suitable example of the dopamine agonist is bromocriptine. Suitable examples of the DPP-4 inhibitor include, but are not limited to, alogliptin, linagliptin, saxagliptin, sitagliptin, and simvastatin. Suitable examples of the GLP-1 include, but are not limited to, lixisenatide, albiglutide, dulaglutide, exenatide, and liraglutide. Suitable examples of the SGLT 2 inhibitor include, but are not limited to, dapagliflozin, canagliflozin, and empagliflozin. Suitable examples of the sulfonylurea include, but are not limited to, glimepiride, gliclazide, glipizide, glyburide, chlorpropamide, tolazamide, and tolbutamide. Suitable examples of the thiazolidinedione include, but are not limited to, pioglitazone and rosiglitazone.

In the present disclosure, the diseases and/or disorders associated with hyperglycemia may be diabetes, obesity, impaired glucose tolerance, impaired fasting glycemia (IFG), hyperinsulinemia, hyperlipidemia, hyper-cholesterolemia, hypertriglyceridemia, lipid metabolism disorder, atherosclerosis, hypertension, congestive heart failure, edema, hyperuricemia, gout, diabetic complication and the like.

According to some embodiments of the present disclosure, the diseases and/or disorders associated with hyperglycemia is diabetes, which includes, but not limited to, type 1 or 2 diabetes, and gestational diabetes. According to one preferred embodiment, the diseases and/or disorders associated with hyperglycemia treatable by the present method is type 2 diabetes.

According to other embodiments of the present disclosure, the diseases and/or disorders associated with hyperglycemia is the diabetic complication, which may be retinopathy, neuropathy, nephropathy, ulcer, or macroangiopathy.

The amount, route of administration and dosing schedule of the compound of formula (I) will depend upon factors such as the specific indication to be treated, prevented, or managed, and the age, sex and condition of the patient. The roles played by such factors are well known in the art, and may be accommodated by routine experimentation.

4. Pharmaceutical Formulation

This invention encompasses pharmaceutical compositions for the treatment or prophylaxis of a disease and/or disorder associated with hyperglycemia. The pharmaceutical composition comprises a therapeutically or prophylactic effective amount of a compound of formula (I) of the present invention.

The compound of formula (I) is present at a level of about 0.1% to 99% by weight, based on the total weight of the pharmaceutical composition. In some embodiments, the compound of formula (I) is present at a level of at least 1% by weight, based on the total weight of the pharmaceutical composition. In certain embodiments, the compound of formula (I) is present at a level of at least 5% by weight, based on the total weight of the pharmaceutical composition. In still other embodiments, the compound of formula (I) is present at a level of at least 10% by weight, based on the total weight of the pharmaceutical composition. In still yet other embodiments, the compound of formula (I) is present at a level of at least 25% by weight, based on the total weight of the pharmaceutical composition.

In some preferred embodiments, the pharmaceutical composition further comprises a blood sugar reducing agent. The blood sugar reducing agent may be selected from the group consisting of, alpha-glucosidase inhibitor, biguanide, dopamine agonist, dipeptidyl peptidase-4 (DPP-4) inhibitor, glucagon-like peptide-1 (GLP-1), meglitinide, sodium glucose transporter (SGLT) 2 inhibitor, sulfonylurea, and thiazolidinedione.

According to one embodiment of the present disclosure, the pharmaceutical composition further comprises the alpha-glucosidase inhibitor, which may be acarbose or miglitol.

According to another embodiment of the present disclosure, the pharmaceutical composition further comprises the biguanide, which preferably is metformin.

According to still another embodiment of the present disclosure, the pharmaceutical composition further comprises the dopamine agonist, which may be bromocriptine.

According to a further embodiment of the present disclosure, the pharmaceutical composition further comprises the DPP-4 inhibitor, and examples of the DPP-4 inhibitor include, but are not limited to, alogliptin, linagliptin, saxagliptin, sitagliptin, and simvastatin.

According to other embodiment of the present disclosure, the pharmaceutical composition further comprises GLP-1. Suitable examples of GLP-1 include, but are not limited to, lixisenatide, albiglutide, dulaglutide, exenatide, and liraglutide.

According to yet another embodiment of the present disclosure, the pharmaceutical composition further comprises SGLT 2 inhibitor. Suitable examples of the SGLT 2 inhibitor include, but are not limited to, dapagliflozin, canagliflozin, and empagliflozin.

According to further embodiment of the present disclosure, the pharmaceutical composition further comprises the sulfonylurea. Suitable examples of the sulfonylurea include, but are not limited to, glimepiride, gliclazide, glipizide, glyburide, chlorpropamide, tolazamide, and tolbutamide.

According to still further embodiment of the present disclosure, the pharmaceutical composition further comprises thiazolidinedione, which may be pioglitazone or rosiglitazone.

Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intra-arterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration requires enteric coatings to protect the compounds of this invention from degradation within the gastrointestinal tract. Similarly, a formulation may contain ingredients that facilitate delivery of the active ingredient(s) to the site of action. For example, compounds may be administered in liposomal formulations, in order to protect them from degradative enzymes, facilitate transport in circulatory system, and effect delivery across cell membranes to intracellular sites.

Similarly, poorly soluble compounds may be incorporated into liquid dosage forms (and dosage forms suitable for reconstitution) with the aid of solubilizing agents, emulsifiers and surfactants such as, but not limited to, cyclodextrins (e.g., α-cyclodextrin or β-cyclodextrin), and non-aqueous solvents, such as, but not limited to, ethyl alcohol, isopropyl alcohol, ethyl carbonate, ethyl acetate, benzyl alcohol, benzyl benzoate, propylene glycol, 1,3-butylene glycol, dimethyl formamide, dimethyl sulfoxide (DMSO), biocompatible oils (e.g., cottonseed, groundnut, corn, germ, olive, castor, and sesame oils), glycerol, tetrahydrofurfuryl alcohol, polyethylene glycols, fatty acid esters of sorbitan, and mixtures thereof (e.g., DMSO:corn oil).

The composition, shape, and type of a dosage form will vary depending on its use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990).

4.1 Oral Dosage Forms

Pharmaceutical compositions of the present invention suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See, e.g., *Remington's Pharmaceutical Sciences,* 18th ed., Mack Publishing, Easton Pa. (1990).

Typical oral dosage forms are prepared by combining the active ingredient(s) in an intimate admixture with at least one excipient according to conventional pharmaceutical compounding techniques. Excipients can take a wide variety of forms depending on the form of preparation desired for administration.

Because of their ease of administration, tablets and capsules represent the most advantageous oral dosage unit forms. If desired, tablets can be coated by standard aqueous or non-aqueous techniques. Such dosage forms can be prepared by conventional methods of pharmacy. In general, pharmaceutical compositions and dosage forms are prepared by uniformly and intimately admixing the active ingredients with liquid carriers, finely divided solid carriers, or both, and then shaping the product into the desired presentation if necessary. Dis-integrants may be incorporated in solid dosage forms to facility rapid dissolution. Lubricants may also be incorporated to facilitate the manufacture of dosage forms (e.g., tablets).

4.2 Parenteral Dosage Forms

Parenteral dosage forms can be administered to patients by various routes including, but not limited to, subcutaneous, intravenous (including bolus injection), intramuscular, and intra-arterial. Because their administration typically bypasses patients' natural defenses against contaminants, parenteral dosage forms are specifically sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: water; aqueous vehicles such as, but not limited to, sodium chloride solution, Ringer's solution, and Dextrose; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

4.3 Transdermal, Topical and Mucosal Dosage Forms

Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences,* 18th eds., Mack Publishing, Easton Pa. (1990). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms are well known to those skilled in the pharmaceutical arts, and depend on the particular tissue to which a given pharmaceutical composition or dosage form will be applied.

Depending on the specific tissue to be treated, additional components may be used prior to, in conjunction with, or subsequent to treatment with active ingredients of the invention. For example, penetration enhancers may be used to assist in delivering active ingredients to the tissue.

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates may also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition 5. Kits Also encompasses within the present disclosure are kits useful for treatment or prophylaxis of a disease and/or disorder associated with hyperglycemia in a subject.

The Kit according to present disclosure include, at least, a first container containing a blood sugar reducing agent, a second container containing the present compound of formula (I); and a legend associated with the kit for instructing a user how to use the kit. The legend may be in a form of pamphlet, tape, CD, VCD or DVD. Examples of the container include, but are not limited to, vials, tubes, and the like.

The present invention will now be described more specifically with reference to the following embodiments, which are provided for the purpose of demonstration rather than limitation. While they are typically of those that might be used, other procedures, methodologies, or techniques known to those skilled in the art may alternatively be used.

EXAMPLES

Materials and Methods
Cell Culture

The RINm5F cells and H460 were grown in manufactures' suggested medium supplemented with 10% heat-inactivated fetal bovine serum, 100 units/mL penicillin, and 100 µg/mL streptomycin, at 37° C. in a humidified 5% $CO_2$ incubator.

cAMP Assay

Real time intracellular cAMP assay was performed as described previously (Cheng et al., J. Biol Chem. 290, 14302-14313 (2015)). Briefly, RINm5F cells stably expressing the RG-cAMP protein were seeded at a density of $3\times10^4$ cells/well in 96-well plates in 0.15 ml of RPMI 1640 medium containing 400 µg/ml G418. Next day, cells were washed twice with 0.1 ml phenol red-free MEM containing 5 mM HEPES, and incubated in the same medium for 1 h. The medium was replaced with 90 µL the same medium containing 1 mg/ml BSA and 5 µM DeepBlueC. The whole plate was immediately loaded onto a SpectraMax Paradigm Detection Platform equipped with a Dual-Color luminescence detection cartridge and SoftMax Pro 6.2.2 (Molecular Devices, Sunnyvale, Calif.) to obtain the background BRET signal based on the sequential integration of the luminescence detected at 370-450 and 500-530 nm over 60-150 s. Each well was then stimulated by adding 10 µl of 10× solutions of peptide and lipids and 1 mg/ml BSA in phenol red-free MEM containing 5 mM HEPES, and BRET signals were obtained immediately under identical settings. The BRET ratio is the ratio of light emitted between 90 and 300 s at 500-530 nm to that emitted at 370-450 nm. The cAMP response was expressed as a percentage of cAMP production, and was calculated as 100×(BRET ratio from 0.01 GLP-1(7-36)-amide–BRET ratio from indicated concentration of peptide with or without lipids)/(BRET ratio from 0.01 nM GLP-1(7-36)-amide–BRET ratio from 250 nM GLP-1(7-36)-amide). The dose-response curve, maximal response, and concentration of peptide needed to yield half-maximal response (EC50) were obtained by nonlinear regression to fit the data to the agonist versus response equation using Prism software 5.0 (GraphPad, San Diego). Unless specified, all cAMP response data are the means±S.E. from three independent experiments with triplicate assays.

Receptor Endocytosis Assay.

U2OS osteosarcoma cell line stably expressing a β-arrestin2:GFP fusion protein was obtained from Norak Biosciences. The pcDNA3 GLP-1R-V2R chimeric construct contains the first 440 amino acids of the GLP-1R (Met-1 to Thr-440) fused to the last 29 amino acids of the vasopressin V2 receptor (Ala-343 to Ser-371) and separated by two alanine residues as linker. GLP-1R-V2R chimeric construct was inserted into the EcoRI site of pcDNA3 (pcDNA3-GLP-1R-V2R) such that expression of the chimeric protein was under the control of the CMV promoter. pcDNA3-GLP-1R-V2R was used to transfect U2OS osteosarcoma cells stably expressing β-arrestin2:GFP to obtain a cell line stably co-expressing GLP-1R-V2R and β-arrestin2:GFP. High content imaging of receptor endocytosis in cells was conducted with 0.03 to 0.001 mg/ml of the test compound to identify potentiating activity for GLP-1-dependent GLP-1R endocytosis. Three replicate 384-well assay microplates were plated with U2OS cells stably co-expressing GLP-1R-V2R and β-arrestin2: GFP at a density of $3\times10^3$ cells/well. Aliquots of 2.5 µl of 10× stocks of the indicated concentration of the test compound in phenol red-free MEM containing increasing concentrations (0.12 to 3,000 nM) of GLP-1(7-36)-amide and 1 mg/ml BSA were transferred to each well of the assay plate, which contained 22.5 µl of phenol red-free MEM containing 1 mg/ml BSA. The three assay plates were incubated at room temperature for 60 min before cell fixation with 2% formaldehyde and labeling of the cell nuclei with 5 µg/ml of the DNA-binding dye Hoechst 33342 for 1 h. Plates were washed twice with PBS and sealed; plates were used immediately.

Imagine and Analysis

Images were acquired on an XL model of the ImageXpress® Micro System (Molecular Devices, Sunnyvale, Calif.) and analyzed with MetaXpress High-Content Image Acquisition and Analysis Software (Molecular Devices, Sunnyvale, Calif.) using the granularity and variable grain analysis modules. MetaXpress was used to retrieve images using DAPI (to retrieve the blue fluorescent Hoechst 33342-labeled nuclear images) and FITC (to retrieve the green fluorescent GFP-β-arrestin images) filter sets and a Plan Fluor ELWD objective. A 20×0.45-numerical aperture microscope objective was used for the imaging, two fields were imaged per well. The number of spots, total area covered by spots, average and integrated fluorescence intensity of the spots, and nuclear area and fluorescence intensity were logged into the database. Data from abnormal cells for which the values were above threshold (abnormal: average nuclear staining intensity <500; integrated fluorescence intensity of area covered by spots <150) were ruled out using Acuity Xpress, followed by selection of the measurement method, spot fluorescence integrated intensity to calculate the average number of spots per nucleus. Dose-response curve, maximal response, and the concentration needed to yield half-maximal response were obtained using nonlinear regression to fit the data to the agonist versus response equation with Prism software 5.0. The extent of receptor endocytosis response was expressed as percent of that elicited by 750 MGLP-1(7-36)-amide.

Cell Viability Test

Cytotoxicity of H460 cells to various compounds was assessed using PrestoBlue® reagent, which was modified by the reducing environment of the viable cell and turns from blue to red in color. In brief, 3,000 H460 cells were seeded with 0.1 ml of RPMI 1640 medium in each well of a 96-well plate and incubated at 37° C. for 24 h before compound treatment. After a 72-h compound treatment, PrestoBlue™ cell viability reagent (Invitrogen) was added to each well according to the manufacturer's protocol. The plates were further incubated in the dark at 37° C. in 5% $CO_2$ for 10 min, and absorbance of all wells was read at both the 570- and 600-nm wavelengths using automatic enzyme-linked immunosorbent assay plate reader (Molecular Devices, Union City, Calif.). The raw data were normalized and corrected according to the manufacturer's protocol. All samples were tested in triplicate, and each test was repeated three times. Cell viability was calculated using the following formula: percent of 100×(average corrected values of compound treated cells)/(average corrected values of untreated cells).

Example 1 Preparation of Exemplary Compounds of Formula (I)

1.1 Synthesis of Compounds of Formula (I-1)

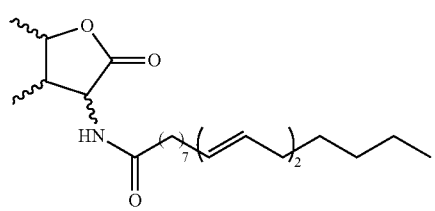
(I-1)

Step 1:

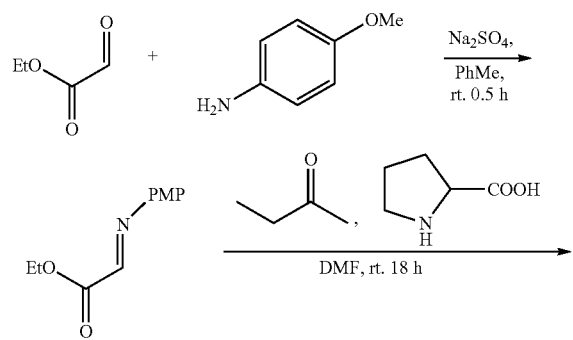

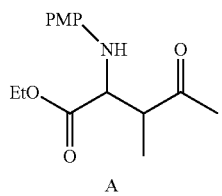

Ethyl 2-(4-Methoxyphenylamino)-3-methyl-4-oxopentanoate (A)

$Na_2SO_4$ (10.7 g, 75.0 mmol) was added to a stirred solution of 4-anisidine (3.69 g, 30.0 mmol) in toluene (PhMe) (30.0 mL), followed by the addition of ethyl glyoxalate (6.13 mL, 30.0 mmol, 50% in toluene) within 10 to 20 min. The reaction mixture was stirred at room temperature for 30 min. After the starting material was consumed, $Na_2SO_4$ was filtered out by Celite, and the filtrate was concentrated under reduced pressure to give a brown oil that was used immediately for the next step without further purification. A solution of the brown oil in dry dimethylformamide (DMF) (15.5 mL) was slowly added to a stirred solution of butanone (59.0 mL, 660 mmol) and proline (1.21 g, 10.5 mmol) in dry DMF (46.6 mL) over 30 min at room temperature, and the resulting mixture was stirred at room temperature for 12 h. After the starting material was consumed, the reaction mixture was filtered through a pad of sieve and concentrated under reduced pressure. The resulting yellow oil was directly used for the next reaction without further purification. A small amount of mixture was applied to column chromatography (silica gel, EtOAc/hexane=1/4) and then HPLC for the characterization of the compound (A). Rf=0.25 (EtOAc/hexane=1/5, UV); IR (film) v=3379, 2981, 2936, 1729, 1713, 1514, 1235, 1200, 1180, 1035, 823 $cm^{-1}$; $^1H$ NMR (400 MHz, $CDCl_3$) δ 6.77 (d, J=8.8 Hz, 2H), 6.66 (d, J=8.8 Hz, 2H), 4.31 (d, J=5.8 Hz, 1H), 4.19-4.13 (m, 2H), 3.74 (s, 3H), 3.03 (m, 1H), 2.23 (s, 3H), 1.25 (d, J=7.1 Hz, 3H), 1.22 (t, J=7.2, 3 H); $^{13}C$ NMR (125 MHz, $CDCl_3$) 209.3, 172.9, 153.3, 140.9, 116.0, 115.0, 61.5, 59.8, 55.8, 49.4, 28.6, 14.3, 12.4.

Step 2:

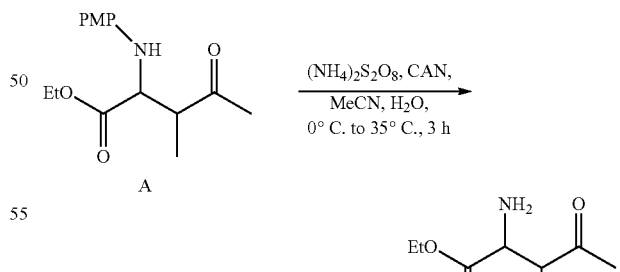

Ethyl-2-Amino-3-methyl-4-oxopentanoate (B)

A solution of $(NH_4)_2S_2O_8$ (913 mg, 4.0 mmol) and cerium ammonium nitrate (CAN) (110 mg, 0.2 mmol) in $H_2O$ (5.8 mL) was slowly added to a stirred solution of the mixture from Step 1, the compound (A) (547 mg, 2.0 mmol) in acetonitrile (MeCN) (1.0 mL) at 0° C. The resulting mixture was then heated to 35° C. and stirred for 3 h. Upon the completion of the reaction, the reaction mixture was diluted with H$_2$O (5.8 mL) and washed with CH$_2$Cl$_2$ (5 mL×4). The aqueous layer was basified with 1 M Na$_2$CO$_3$ aqueous solution to pH~8 and then extracted with CH$_2$Cl$_2$ (15 mL×5). The combined organic layers were dried over Na$_2$SO$_4$ and concentrated under reduced pressure to give a brown liquid that contains the compound (B) (229 mg). The crude mixture was used immediately for the next reaction without further purification. Characterization of the compound (B): Rf=0.40 (methanol/CH$_2$Cl$_2$=1/10, ninhydrin); $^1$H NMR (400 MHz, CDCl$_3$) δ 4.19-4.13 (m, 2H), 3.86 (d, J=4.8 Hz, 1H), 2.91 (m, 1H), 2.19 (s, 3H), 1.25 (t, J=7.1 Hz, 3H), 1.11 (d, J=7.2 Hz, 3H); $^{13}$C NMR (100 MHz, CDCl$_3$) δ 209.9, 174.3, 61.3, 55.4, 49.8, 28.4, 14.2, 11.0; HRMS (APCI-TOF) m/z [M+H]+ calcd. for C$_8$H$_{16}$O$_3$N 174.1130, found 174.1127.

Step 3:

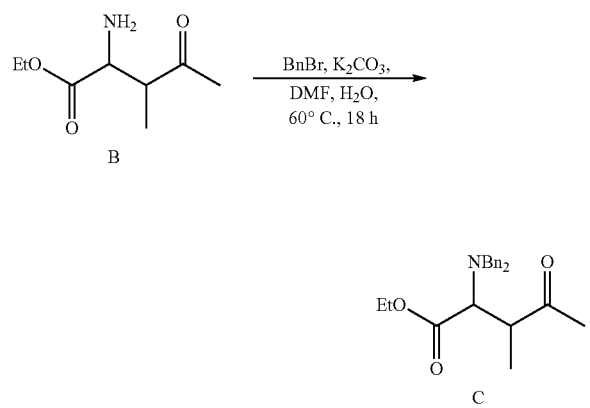

Ethyl 2-(Dibenzylamino)-3-methyl-4-oxopentanoate (C)

A suspension of the crude mixture from Step 2, the compound (B) (98 mg, 0.57 mmol) and K$_2$OC$_3$ (235 mg, 1.7 mmol) in DMF/H$_2$O (1.1 mL/0.11 mL) was stirred at room temperature for 15 min, followed by the dropwise addition of benzyl bromide (BnBr) (0.34 mL, 2.8 mmol). After stirring at 60° C. for 18 h, H$_2$O (5 mL) was added, and the reaction mixture was then extracted with EtOAc (10 mL×3). The combined organic layers were dried over Na$_2$SO$_4$ and concentrated under reduced pressure. The residue was purified by flash column chromatography on silica gel (EtOAc/hexane=1/15) to give the compound (C) as a white solid (120 mg, 0.34 mmol, 60%). Rf=0.45 (EtOAc/hexane=1/5, UV); mp 58.8-62.3° C.; IR (film) v=3062, 3029, 2977, 2929, 2852, 1723, 1602, 1495, 1454, 1370, 1201, 1169, 1026, 961, 748, 699 cm$^{-1}$; $^1$H NMR (400 MHz, CDCl$_3$) δ 7.37-7.22 (m, 10H), 4.34-4.16 (m, 2H), 3.86 (d, J=13.5 Hz, 2H), 3.49 (d, J=10.9 Hz, 1H), 3.45 (d, J=13.4 Hz, 2H), 3.08 (dt, J=10.9, 7.2 Hz, 1H), 2.15 (s, 3H), 1.38 (t, J=7.1 Hz, 3H), 1.10 (d, J=7.3 Hz, 3H); $^{13}$C NMR (100 MHz, CDCl$_3$) δ 211.5, 171.9, 138.9, 129.2, 128.4, 127.3, 62.6, 60.5, 55.2, 46.0, 29.2, 14.7, 14.5; HRMS (ESI-TOF) m/z [M+H]+ calcd. for C$_{22}$H$_{28}$O$_3$N 354.2069, found 354.2061.

Step 4:

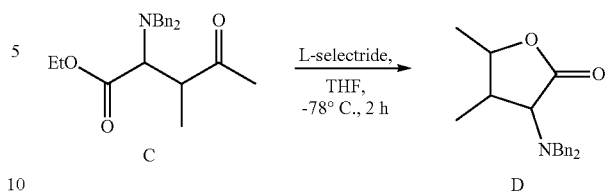

3-(Dibenzylamino)-4,5-dimethyldihydrofuran-2(3H)-one (D)

L-selectride [0.54 mL, 1.0 M in tetrahydrofuran (THF), 0.54 mmol] was added to a stirred solution of the compound (C) (173 mg, 0.49 mmol) in dry THF (4.9 mL) at −78° C. under nitrogen. After stirring for 2 h at −78° C., the reaction mixture was poured into a vigorously stirred mixture of EtOAc/1 M HCl aqueous solution (10.0 mL/10.0 mL). The aqueous layer was extracted with EtOAc (10 mL×3). The combined organic layers were washed with H$_2$O (5 mL×3-5) until pH~6 and then washed with brine, dried over Na$_2$SO$_4$, and concentrated under reduced pressure. The residue was purified by flash column chromatography on silica gel (EtOAc/hexane=1/20, UV) to give the compound (D) as a white solid (143 mg, 0.46 mmol, 94%). Rf=0.33 (EtOAc/hexane=1/10, UV); mp 66.5-69.7° C.; IR (film) v=3062, 3028, 2972, 2928, 2850, 1769, 1601, 1493, 1454, 1385, 1325, 1236, 1185, 1171, 1141, 1050, 995, 953, 745, 699 cm$^{-1}$; $^1$H NMR (400 MHz, CDCl$_3$) δ 7.42-7.40 (m, 4H), 7.35-7.31 (m, 4H), 7.28-7.23 (m, 2H), 4.00 (d, J=13.8 Hz, 2H), 3.91-3.83 (m, 3H), 3.29 (d, J=11.8 Hz, 1H), 2.05 (m, 1H), 1.35 (d, J=6.1 Hz, 3H), 1.02 (d, J=6.5 Hz, 3H); $^{13}$C NMR (100 MHz, CDCl$_3$) δ 175.3, 139.4, 128.8, 128.4, 127.3, 79.6, 65.4, 54.9, 42.1, 18.9, 14.1; HRMS (ESI-TOF) m/z [M+Na]+ calcd. for C$_{20}$H$_{23}$O$_2$NNa 332.1626, found 332.1623.

Step 5:

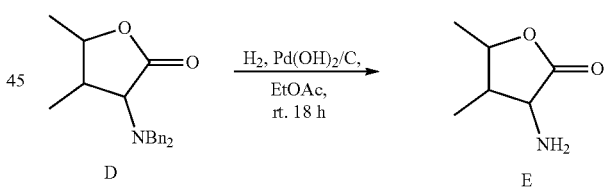

3-Amino-4,5-dimethyldihydrofuran-2(3H)-one (E)

Pd(OH)$_2$/C (6.2 mg, 20%) was added to a stirred solution of the compound (D) (61.9 mg, 0.20 mmol) in EtOAc (4.0 mL) under nitrogen and then purged with hydrogen (1 atm, balloon) for an hour at room temperature. After stirring at room temperature under hydrogen for 18 h, the reaction mixture was filtered through Celite and concentrated under reduced pressure to give the compound (E) as a colorless oil (25.8 mg, 0.20 mmol, >99%) without further purification. Rf=0.4 (methanol/CH$_2$Cl$_2$=1/10, ninhydrin); IR (film) v=3374, 3310, 2973, 2927, 2878, 2852, 1771, 1456, 1389, 1330, 1192, 1145, 1044, 983, 946, 918, 735, 702 cm$^{-1}$; $^1$H NMR (400 MHz, CDCl$_3$) δ 4.05 (dq, J=9.9, 6.1 Hz, 1H), 3.25 (d, J=5.2 Hz, 1H), 1.80 (m, 1H), 1.73 (s, 2H), 1.42 (d, J=6.2 Hz, 3H), 1.21 (d, J=6.6 Hz, 3H); $^{13}$C NMR (100 MHz, CDCl₃) δ 178.2, 79.8, 58.9, 47.5, 18.6, 14.2; HRMS (EI+) m/z M+calcd. for $C_6H_{11}O_2N$ 129.0790, found 129.0791.

Step 6:

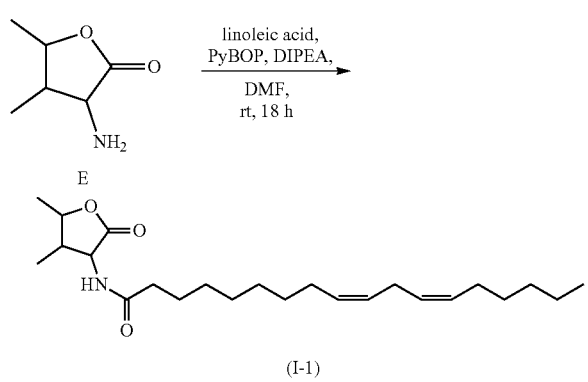

(9Z,12Z)-N-(4,5-Dimethyl-2-oxotetrahydrofuran-3-yl)octadeca-9,12-dienamide (I-1)

Benzotriazol-1-oxytripyrrolidinophosphonium hexafluorophosphate (PyBOP) (62.5 mg, 0.12 mmol) was added to a stirred solution of the compound (E) (12.9 mg, 0.10 mmol) and linoleic acid (31 μL, 0.10 mmol) in dry DMF (1.0 mL), followed by freshly distilled N,N-diisopropylethylamine (DIPEA) (21 μL, 0.12 mmol) at room temperature under nitrogen. The reaction mixture was stirred for 18 h. After the starting material was consumed, the reaction mixture was diluted with EtOAc (10 mL) and washed with H2O (5 mL) and brine (5 mL). The organic layer was dried over $Na_2SO_4$ and concentrated under reduced pressure. The residue was purified by flash column chromatography on silica gel (EtOAc/hexane=1/4) to give the compound (I-1) as a colorless oil (36.9 mg, 0.094 mmol, 94%). Rf=0.28 [ethyl acetate (EtOAc)/hexane=1/2, I2]; IR (film) v=3303, 3009, 2957, 2927, 2855, 1782, 1657, 1650, 1533, 1461, 1454, 1389, 1187, 1047, 908, 723 cm⁻¹; ¹H NMR (500 MHz, CD₃OD) δ 5.39-5.29 (m, 4H), 4.38 (d, J=11.8 Hz, 1H), 4.19 (dt, J=9.8, 6.1 Hz, 1H), 2.78 (t, J=6.5 Hz, 2H), 2.26 (t, J=7.5 Hz, 2H), 2.17-2.04 (m, 5H), 1.66-1.60 (m, 2H), 1.41 (d, J=6.1 Hz, 3H), 1.40-1.28 (m, 14H), 1.13 (d, J=6.6 Hz, 3H), 0.91 (t, J=6.9 Hz, 3H); ¹³C NMR (125 MHz, CD₃OD) δ 176.5, 176.2, 130.9, 130.9, 129.1, 129.1, 81.4, 57.5, 45.6, 36.9, 32.7, 30.7, 30.5, 30.3, 30.3, 30.2, 28.2, 26.8, 26.5, 23.6, 18.8, 14.4, 14.0; HRMS (MALDI-TOF) m/z [M+Na]+ calcd. for $C_{24}H_{41}O_3NNa$ 414.2979, found 414.2963.

1.2 Synthesis of Compound of Formula (I-11)

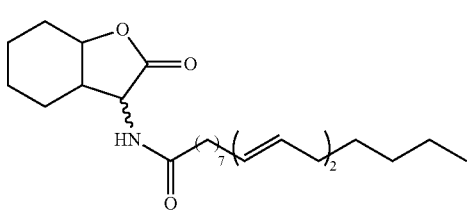

Step 1:

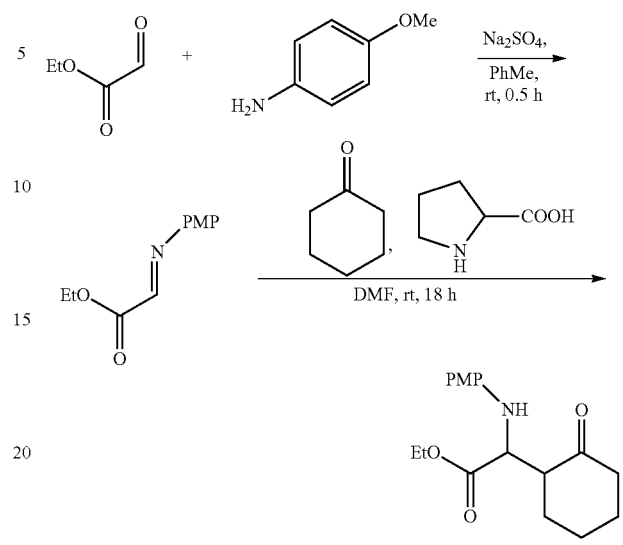

Ethyl 2-(4-Methoxyphenylamino)-2-(2'-oxocyclohex-1'-yl)acetate (I-11-i)

$Na_2SO_4$ (1.77 g, 12.5 mmol) was added to a stirred solution of 4-anisidine (616 mg, 5.0 mmol) in toluene (PhMe) (5.0 mL), followed by the addition of ethyl glyoxalate (1.02 mL, 5.0 mmol, 50% in toluene) within 10 to 20 min. The reaction mixture was stirred at room temperature for 30 min. After the starting material was consumed, $Na_2SO_4$ was filtered out by Celite, and the filtrate was concentrated under reduced pressure to give a brown oil that was used immediately for the next step without further purification. A solution of the brown oil in dry dimethylformamide (DMF) (2.6 mL) was slowly added to a stirred solution of cyclohexanone (8.4 mL, 110 mmol) and proline (201 mg, 1.75 mmol) in dry DMF (7.8 mL) over 30 min at room temperature, and the resulting mixture was stirred at room temperature for 12 h. After the starting material was consumed, the reaction mixture was filtered through a pad of sieve and concentrated under reduced pressure. The residue was purified by flash column chromatography on silica gel (EtOAc/hexane=1/5) to give the compound (I-11-i) as an orange solid (1.24 g, mmol, 81%). Rf=0.45 (EtOAc/hexane=1/2, UV); ¹H NMR (400 MHz, CDCl₃) δ 6.78-6.71 (m, 4H), 4.23 (d, J=4.9 Hz, 1H), 4.19-4.10 (m, 2H), 3.90 (br-s, 1H), 3.73 (s, 3H), 2.80 (m, 1H), 2.48-2.44 (m, 1H), 2.35-2.26 (m, 1H), 2.22-2.04 (m, 1H), 1.96-1.93 (m, 1H), 1.86-1.67 (m, 4H), 1.21 (t, J=7.2 Hz, 3H); ¹³C NMR (100 MHz, CDCl₃) δ 210.1, 173.5, 153.2, 141.3, 116.2, 114.9, 61.2, 58.2, 55.8, 53.7, 41.9, 29.7, 26.9, 24.9, 14.2.

Step 2:

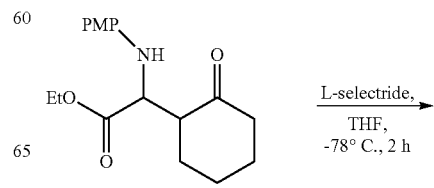

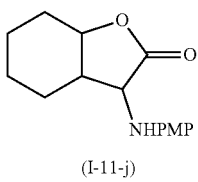

(I-11-j)

3-(4-Methoxyphenylamino)hexahydrobenzofuran-2(3H)-one (I-11-j)

L-selectride [0.55 mL, 1.0 M in tetrahydrofuran (THF), 0.55 mmol] was added to a stirred solution of the compound (I-11-i) (153 mg, 0.50 mmol) in dry THF (5.0 mL) at −78° C. under nitrogen. After stirring for 2 h at −78° C., the reaction mixture was poured into a vigorously stirred mixture of EtOAc/1 M HCl aqueous solution (10.0 mL/10.0 mL). The aqueous layer was extracted with EtOAc (10 mL×3). The combined organic layers were washed with H$_2$O (5 mL×3-5) until pH~6 and then washed with brine, dried over Na$_2$SO$_4$, and concentrated under reduced pressure. The residue was purified by flash column chromatography on silica gel (EtOAc/hexane=1/4, UV) to give the compound (I-11-j) as a yellow oil (87 mg, 0.33 mmol, 67%). Rf=0.43 (EtOAc/hexane=1/2, UV); $^1$H NMR (400 MHz, CDCl$_3$) δ 6.78 (d, J=8.8 Hz, 2H), 6.68 (d, J=8.9 Hz, 2H), 4.59 (m, 1H), 3.96 (d, J=8.4 Hz, 1H), 3.74 (s, 3H), 2.44 (m, 1H), 2.04-1.94 (m, 1H), 1.77-1.60 (m, 4H), 1.55-1.48 (m, 2H), 1.40-1.30 (m, 1H); $^{13}$C NMR (100 MHz, CDCl$_3$) δ 176.7, 153.3, 140.9, 115.6, 115.0, 77.0, 57.9, 55.8, 41.8, 29.0, 24.6, 21.5, 21.4.

Step 3:

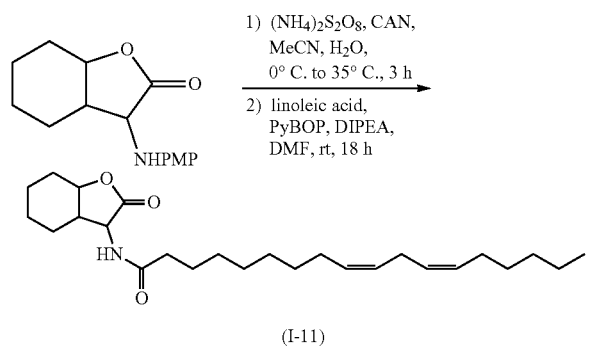

(I-11)

(9Z,12Z)-N-(2-Oxooctahydrobenzofuran-3-yl)octadeca-9,12-dienamide (I-11)

A solution of (NH$_4$)$_2$S$_2$O$_8$ (69.9 mg, 0.31 mmol) and cerium ammonium nitrate (CAN) (8.4 mg, 0.015 mmol) in H$_2$O (0.77 mL) was slowly added to a stirred solution of the compound (I-11-j) (40.0 mg, 0.15 mmol) in acetonitrile (MeCN) (0.6 mL) at 0° C. The resulting mixture was then heated to 35° C. and stirred for 3 h. Upon the completion of the reaction, the reaction mixture was diluted with H$_2$O (2 mL) and washed with CH$_2$Cl$_2$ (2 mL×4). The aqueous layer was basified with 1 M Na$_2$CO$_3$ aqueous solution to pH~8 and then extracted with CH$_2$Cl$_2$ (5 mL×5). The combined organic layers were dried over Na$_2$SO$_4$ and concentrated under reduced pressure to give a crude as a brown liquid (13.1 mg, ~0.084 mmol, ~55%). PyBOP (52.7 mg, 0.10 mmol) was added to a stirred solution of the crude (13.1 mg, ~0.084 mmol) and linoleic acid (26 μL, 0.084 mmol) in dry DMF (0.84 mL), followed by freshly distilled N,N-diisopropylethylamine (DIPEA) (18 μL, 0.10 mmol) at room temperature under nitrogen. The reaction mixture was stirred for 18 h. After the starting material was consumed, the reaction mixture was diluted with EtOAc (10 mL) and washed with H$_2$O (5 mL) and brine (5 mL). The organic layer was dried over Na$_2$SO$_4$ and concentrated under reduced pressure. The residue was purified by flash column chromatography on silica gel (EtOAc/hexane=1/4) to give the compound (I-11) as a colorless oil (29.3 mg, 0.070 mmol, 83%). Rf=0.4 (EtOAc/hexane=1/2, I2); IR (film) ν=3296, 3009, 2927, 2855, 1785, 1657, 1650, 1547, 1536, 1463, 1453, 1175, 1126, 1015, 725 cm$^{-1}$; $^1$H NMR (500 MHz, CDCl$_3$) δ 6.01 (d, J=8.0 Hz, 1H), 5.40-5.29 (m, 4H), 4.92 (dd, J=8.1, 12.3 Hz, 1H), 4.51 (dt, J=10.7, 6.7 Hz, 1H), 2.76 (t, J=6.7 Hz, 2H), 2.48-2.43 (m, 1H), 2.29-2.21 (m, 2H), 2.21-2.17 (m, 1H), 2.06-2.01 (m, 4H), 1.92-1.89 (m, 1H), 1.81-1.78 (m, 1H), 1.71-1.52 (m, 5H), 1.44-1.19 (m, 16H), 0.88 (t, J=6.8 Hz, 3H); $^{13}$C NMR (125 MHz, CDCl$_3$) δ 175.9, 174.1, 130.3, 130.1, 128.1, 128.0, 77.3, 49.7, 42.3, 36.4, 31.6, 29.7, 29.4, 29.4, 29.3, 29.2, 27.3, 25.7, 25.5, 24.2, 22.7, 22.5, 20.0; HRMS (MALDI-TOF) m/z [M+Na]+ calcd. for C$_{26}$H$_{43}$O$_3$NNa 440.3135, found 440.3145.

1.3 Synthesis of Exemplary Compound of Formula (I-10)

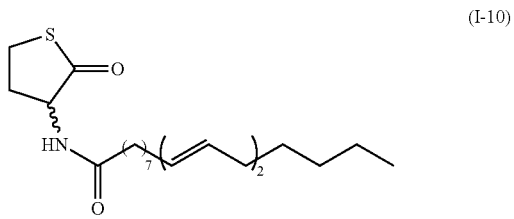

(I-10)

PyBOP (122 mg, 0.23 mmol) was added to a stirred solution of the starting material (I-10-i) (30.0 mg, 0.20 mmol), linoleic acid (61 μL, 0.20 mmol), and freshly distilled DIPEA (75 μL, 0.43 mmol) in dry DMF (2.0 mL) at room temperature under nitrogen. The reaction mixture was stirred for 18 h. After the starting material was consumed, the reaction mixture was diluted with EtOAc (10 mL) and washed with H$_2$O (5 mL) and brine (5 mL). The organic layer was dried over Na$_2$SO$_4$ and concentrated under reduced pressure. The residue was purified by flash column chromatography on silica gel (EtOAc/hexane=1/2) to give the compound (I-10) as a colorless solid (71.0 mg, 0.19 mmol, 96%). Rf=0.45 (EtOAc/hexane=1/1, I2); IR (film) ν=3283, 3008, 2926, 2854, 1711, 1650, 1536, 1462, 1275, 1055, 1019, 916, 724 cm$^{-1}$; $^1$H NMR (500 MHz, CDCl$_3$) δ 5.90 (d, J=4.7 Hz, 1H), 5.41-5.29 (m, 4H), 4.50 (m, 1H), 3.36 (dt, J=5.1, 11.8 Hz, 1H), 3.25 (dd, J=6.8, 11.3 Hz, 1H), 2.97 (m, 1H), 2.76 (t, J=6.6 Hz, 2H), 2.23 (dt, J=2.3, 7.6 Hz, 2H), 2.04 (m, 4H), 1.90 (m, 1H), 1.65-1.60 (m, 2H), 1.38-1.25 (m, 14H), 0.88 (t, J=6.8 Hz, 3H); $^{13}$C NMR (125 MHz, CDCl$_3$) δ 205.8, 173.8, 130.3, 130.1, 128.2, 128.0, 59.6, 36.5, 32.3, 31.6, 29.7, 29.4, 29.3, 29.3, 29.2, 27.7, 27.3, 25.7, 25.6, 22.7, 14.2; HRMS (MALDI-TOF) m/z [M+H]+ calcd. for C$_{22}$H$_{38}$O$_2$NS 380.2614, found 380.2614.

Example 2 Compounds of Formula (I) Enhances GLP-1 Stimulated cAMP Production

In this example, the respective effects of a series of compounds of formula (I), including compounds 1 (or N55), 12, 14, 18, and a racemic mixture of compounds 16 and 17, on GLP-1 induced cAMP production in RINm5F cells were investigated, and results are provided in FIG. 1A to 1E. The data indicated that each of the test compounds may enhance the GLP-1R signaling (i.e., GLP-1 induced cAMP production) in a dose dependent manner (FIG. 1A to 1E).

Example 3 Characterization of Compound 1 (N55)

3.1 Compound 1 Enhances GLP-1R Signaling

Figure 2:
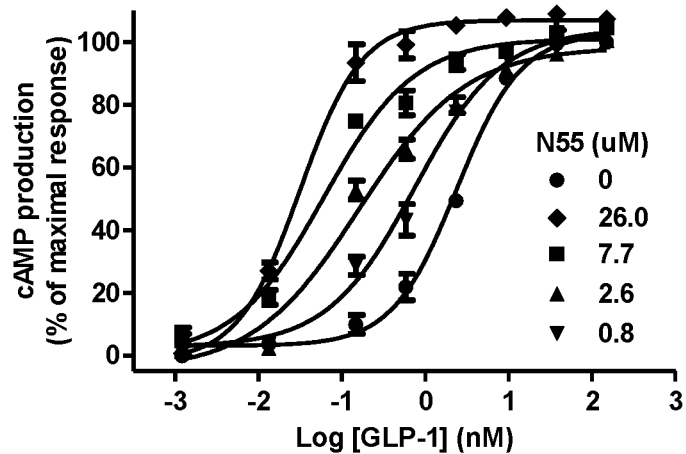
FIG. 2 illustrates the effect of compound 1 (N55) on GLP-1 induced cAMP production in RINm5F cells in according to one embodiment of the present disclosure, (A) Increasing concentration of compound 1 (N55) on cAMP production in response to GLP-1. (B) Compound 1 dose dependently and saturably increases the potency of GLP-1 to stimulate the production of cAMP.
Figure 2:
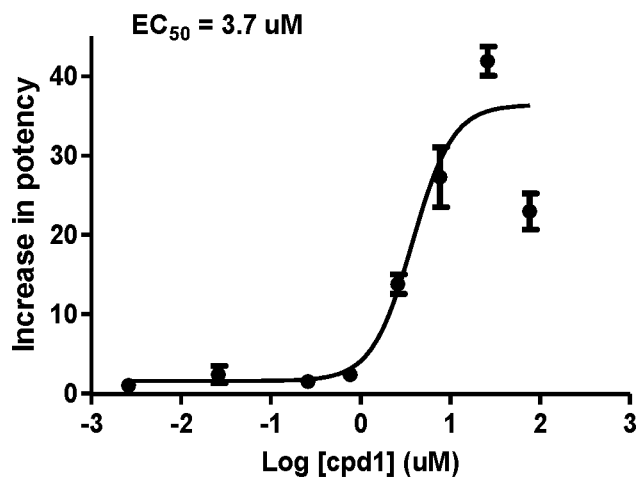
Figure 3:
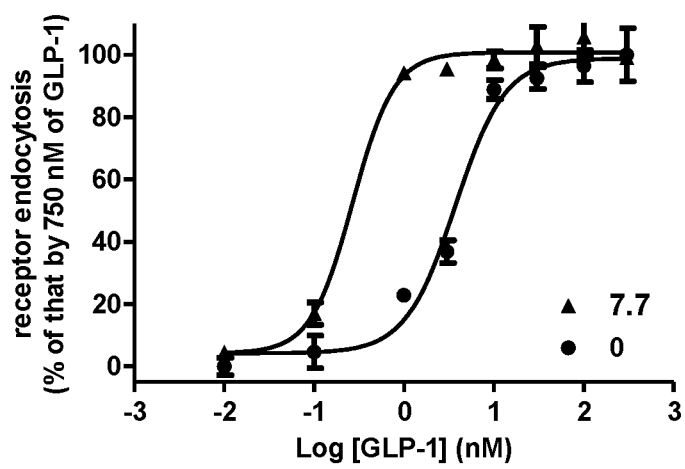
FIG. 3 illustrates the effect of compound 1 on GLP-1 induced GLP-1R endocytosis in according to one embodiment of the present disclosure. (A) Response of GLP-1R endocytosis to the titration of GLP-1 in the absence (circles) or presence (triangles) of 7.7 µM of compound 1. (B) Compound 1 dose-dependently and saturably enhanced GLP-1R endocytosis elicited by 1 nM GLP-1.
Figure 3:
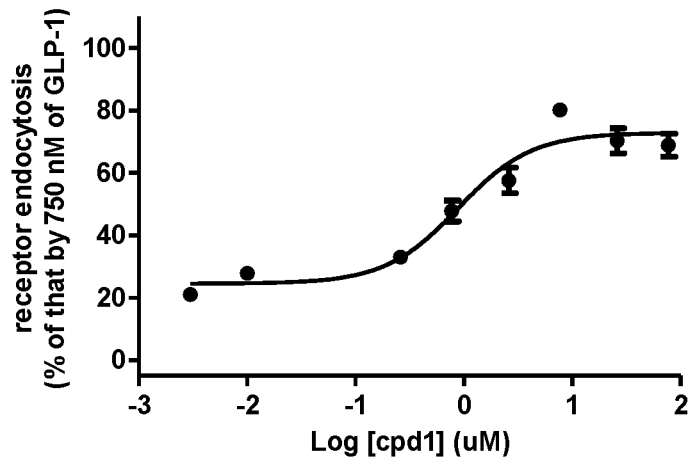

Among the compounds of formula (I) tested in example 2, compound 1 (or N55) seemed to possess the most potency and was chosen for further study in this example, results are illustrated in FIGS. 2 and 3.

GLP-1 induced cAMP production in a dose dependent and saturable manner, with an $EC_{50}$ of 2.4 nM (FIG. 2, panel A). Compound 1 enhanced cAMP production by shifting the dose-response curve to the left >10-fold, and reduced the $EC_{50}$ of GLP-1 by a factor of 40, as the concentration of compound 1 increased from 0.8 μM to 26 μM (FIG. 2, panel A). Compound 1 increased the potency of GLP-1 in a dose dependent and saturable manner, with an $EC_{50}$ of 3.7 μM (FIG. 2, panel B).

To further elucidate the action of compound 1, GLP-1 receptor endocytosis was performed, and results are provided in FIG. 3.

It was found that compound 1 at a concentration of 7.7 μM significantly shifted the dose-response curve of GLP-1 titration to the left and reduced $EC_{50}$ to 0.27 nM (FIG. 3, panel A). The effects of titration of compound 1 (N55) on GLP-1R endocytosis elicited by 1 nM GLP-1 indicated that compound 1 (N55) facilitated GLP-1 stimulation of receptor endocytosis in a dose-dependent and saturable manner (FIG. 3, panel B). $EC_{50}$ required to enhance receptor endocytosis by 1 nM GLP-1 was 0.87 μM.

3.2 Compound 1 Facilitates GLP-1-Elicited Insulin Release from RINm5F Cells

As compound 1 enhanced the potency of GLP-1 through cAMP production, its effect on subsequent insulin release from pancreatic β-cell line RINm5F cells was investigated.

Figure 4:
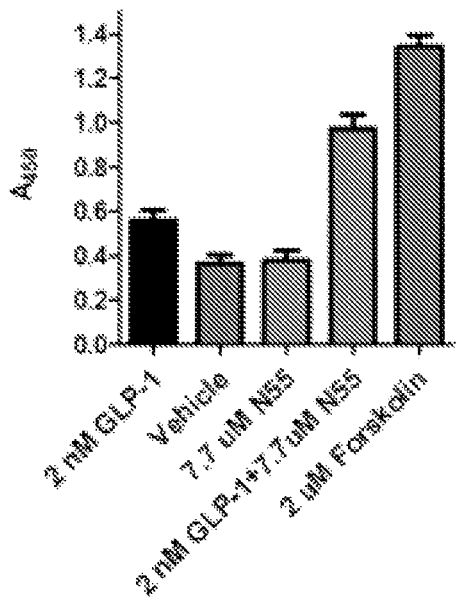
FIG. 4 illustrates the effect of compound 1 on GLP-1 elicited insulin release from RINm5F cells in according to one embodiment of the present disclosure.

It was found that 2 nM GLP-1 consistently stimulated a low level of insulin release from RINm5F cells, and the response was significantly enhanced by the addition of 7.7 μM of compound 1, although compound 1 alone did not trigger any insulin release (FIG. 4). Forskolin was included in this example as a positive control, as it also resulted in the production of cAMP, which led to subsequent insulin release from RINm5F cells.

3.3 Comparison of Compound 1 with Other Fatty Acids on the Potentiation of GLP-1 Induced cAMP Production It is known that the GLP-1 induced cAMP production may be potentiated by various types of fatty acids, accordingly, their effects were respectively compared with that of compound 1, and results are summarized in Table 1.

Among 30 fatty acids that were tested in Table 1, only 3 of them (i.e., eicosanpentaenoyl ethanolamide, linoleoyl ethanolamide, and α-linolenoyl ethanolamide) had activities comparable to that of compound 1 (i.e., about 90% of the activity of compound 1); whereas the efficacies of most fatty acids were in the lower range of that of compound 1 (i.e., 10 to 35% of the activity of compound 1).

TABLE 1

| Name of Compound | Activity % of compound 1 |
| --- | --- |
| Compound 1 (N55) | 100 |
| 9(E),11(E)-conjugated linoleic acid | 30 |
| 10(E),12(Z)-conjugated linoleic acid | 30 |
| Linoelaidic acid | 30 |
| Eicosapentaenoic acid | 60 |
| Docosahexaenoic acid | 60 |
| α-linolenic acid | 15 |
| 9(Z),11(E)-conjugated linoleic acid | 25 |
| Methyl linolelaidate | 30 |
| γ-linoleic acid methyl ester | 25 |
| linolenic acid methyl ester | 15 |
| linoleic acid methyl ester | 30 |
| 11-trans-octadecenoic acid | 10 |
| Cis-octadecenoic acid | 25 |
| Oleic acid | 35 |
| Methyl cis,cis-9,12-octadecadienoate | 15 |
| Methyl γ-linolenate | 20 |
| Docosahexaenoyl ethanolamide | 20 |
| Docosahexaenoyl serotonin | 15 |
| Docosahexaenoyl glycine | 15 |
| 1-monolinolein | 80 |
| Ethyl linoleate | 60 |
| Eicosapentaenoyl ethanolamide | 90 |
| Eicosapentaenoyl serotonin | 20 |
| Linoleoyl glycine | 80 |
| N-(α-linolenoyl) tyrosine | 70 |
| Linoleoyl ethanolamide | 90 |
| α-linolenoyl ethanolamide | 90 |
| 4-hydroxyisoleucine | <10 |

3.4 Compound 1 does not Affect Cell Viability

Figure 5:
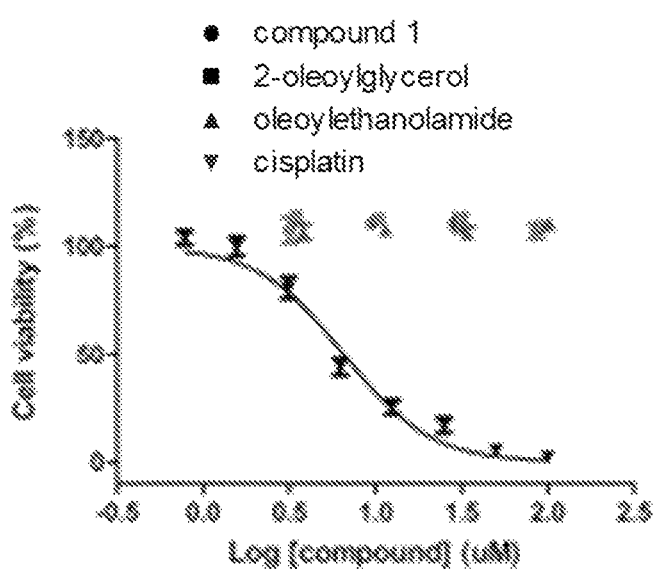
FIG. 5 illustrates the cytotoxicity test of compound 1 in accordance with one embodiment of the present disclosure.

The effect of compound 1 on cell viability was investigated in this example by comparing with that of other agents (e.g., endocannabinoid-like lipids, and anticancer agent), and results are depicted in FIG. 5.

It was found that within the test concentration from 0.78 to 100 μM, compound 1, 2-oleoylglycerol and oleoylethanolamide did not exhibit detectable cytotoxicity, however, cisplatin results in cell death at a concentration of 50 μM, and exhibit an $IC_{50}$ of 6.7 μM (FIG. 5).

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of the present disclosure.

What is claimed is:

1. A compound of formula (I),

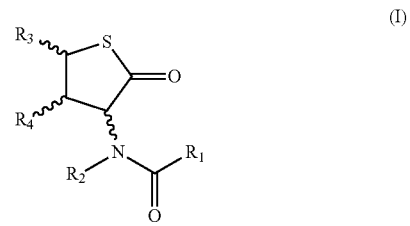

wherein,
X is O or S;
R₁ is

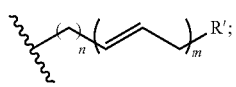

R₂ is H or a nitrogen protecting group;
R₃ and R₄ are independently H, halogen, optionally substituted alkyl, or alkenyl; or R₃ and R₄ are taken together to form an optionally substituted 6-membered carbocycle or heterocycle;
R' is H or optionally substituted alkyl; and
n and m are independently an integral between 1 to 10, provided that when X is O, then R₃ and R₄ are not H; when X is S, then m is not for 4.

2. The compound of claim 1, wherein the compound is selected from the group consisting of:

1

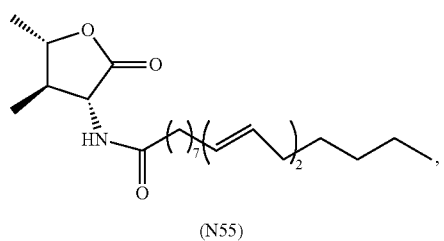

(N55)

2

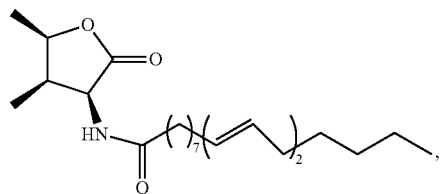

3

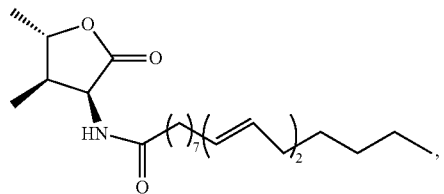

4

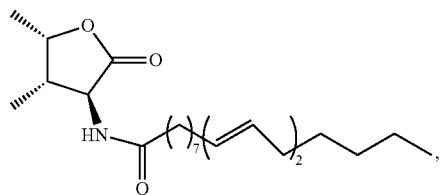

5

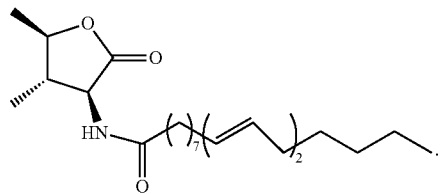

6

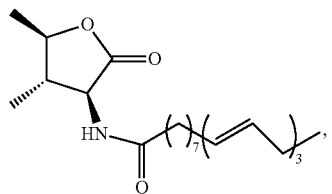

7

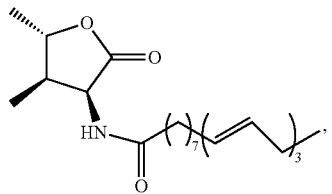

8

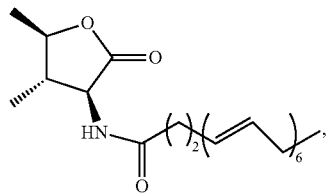

9

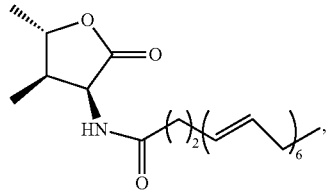

10

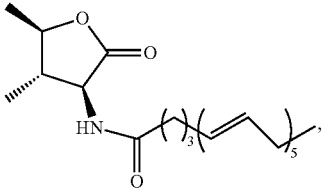

11

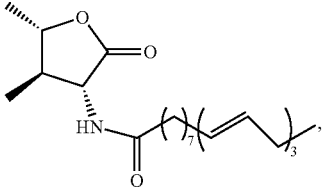

12

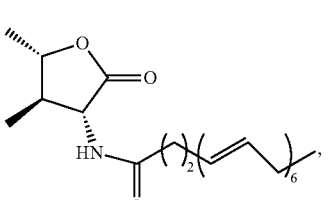

13

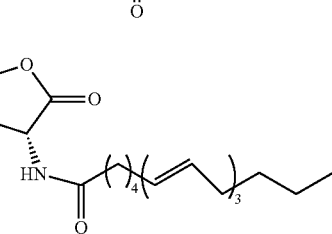

-continued

14
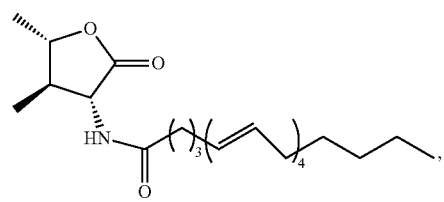

15
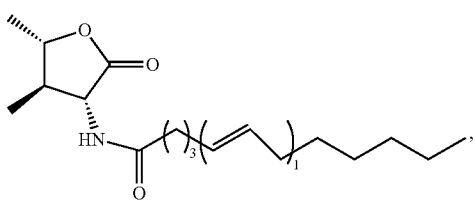

16
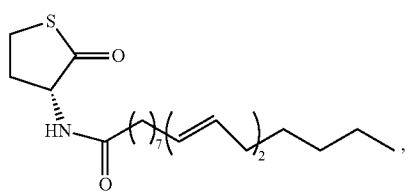

17
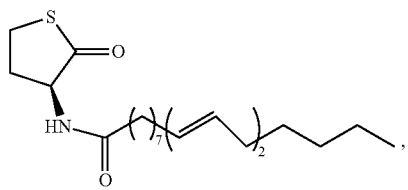

18
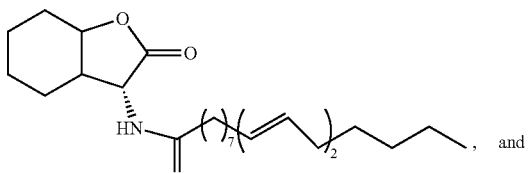

, and

19
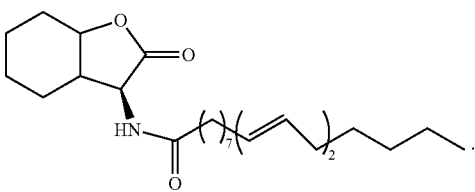

3. The compound of claim 1, wherein the compound is

1
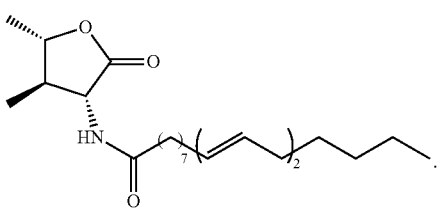

4. A method for treating diseases and/or disorders associated with hyperglycemia in a subject comprising administering to the subject a therapeutically effective amount of the compound of claim 1, so as to reduce the blood sugar level of the subject; wherein the diseases and/or disorders associated with hyperglycemia is diabetes, obesity, impaired glucose tolerance, impaired fasting glycemia (IFG) hyperinsulinemia, hyperlipidemia, hyper-cholesterolemia, hyper-triglyceridemia, lipid metabolism disorder, atherosclerosis, hypertension, congestive heart failure, edema, hyperuricemia, gout or diabetic complication.

5. The method of claim 4, wherein the compound is

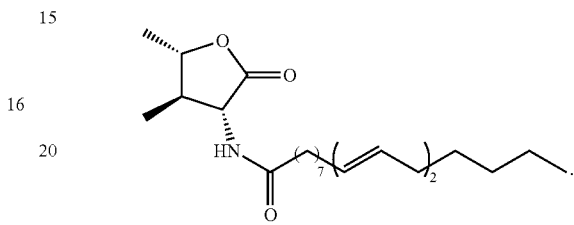

6. The method of claim 4, further comprising administering to the subject a blood sugar reducing agent before, together with, or after the administration of the compound of claim 1.

7. The method of claim 6, wherein the blood sugar reducing agent is selected from the group consisting of, alpha-glucosidase inhibitor, biguanide, dopamine agonist, dipeptidyl peptidase-4 (DPP-4) inhibitor, glucagon-like peptide-1 (GLP-1), meglitinide, sodium glucose transporter (SGLT) 2 inhibitor, sulfonylurea, and thiazolidinedione.

8. The method of claim 7, wherein the alpha-glucosidase inhibitor is acarbose or miglitol.

9. The method of claim 7, wherein the biguanide is metformin.

10. The method of claim 7, wherein the dopamine agonist is bromocriptine.

11. The method of claim 7, wherein the DPP-4 inhibitor is alogliptin, linagliptin, saxagliptin, sitagliptin, or simvastatin.

12. The method of claim 7, wherein the GLP-1 is lixisenatide, albiglutide, dulaglutide, exenatide, or liraglutide.

13. The method of claim 7, wherein the SGLT 2 inhibitor is dapagliflozin, canagliflozin, or empagliflozin.

14. The method of claim 7, wherein the sulfonylurea is glimepiride, gliclazide, glipizide, glyburide, chlorpropamide, tolazamide, or tolbutamide.

15. The method of claim 7, wherein the thiazolidinedione is pioglitazone or rosiglitazone.

16. The method of claim 4, wherein the diabetic complication is retinopathy, neuropathy, nephropathy, ulcer, or macroangiopathy.

* * * * *